United States Patent [19]

Kelman

[11] Patent Number: 4,676,794
[45] Date of Patent: Jun. 30, 1987

[54] INTRAOCULAR LENS

[76] Inventor: Charles D. Kelman, 269 Grand Central Pkwy., Floral Park, N.Y. 11005

[21] Appl. No.: 922,828

[22] Filed: Oct. 22, 1986

Related U.S. Application Data

[63] Continuation of Ser. No. 465,573, Feb. 10, 1983, abandoned.

[51] Int. Cl.⁴ .............................................. A61F 2/16
[52] U.S. Cl. ......................................................... 623/6
[58] Field of Search ............................................. 623/6

[56] References Cited

U.S. PATENT DOCUMENTS

| | | | |
|---|---|---|---|
| 4,174,543 | 11/1979 | Kelman | 623/6 |
| 4,242,760 | 1/1981 | Rainin | 623/6 |
| 4,249,271 | 2/1981 | Poler | 623/6 |
| 4,370,760 | 2/1983 | Kelman | 623/6 |
| 4,403,353 | 9/1983 | Tennant | 623/6 |
| 4,418,431 | 12/1983 | Feaster | 623/6 |
| 4,446,581 | 5/1984 | Blake | 623/6 |
| 4,504,981 | 3/1985 | Walman | 623/6 |
| 4,589,147 | 5/1986 | Nevyas | 623/6 |

OTHER PUBLICATIONS

Lens Styles from Cilco (advertisement brochure), Cilco, Inc., 1616 13th Ave., Box 1680, Huntington, W. Va. 25717, Multiflex Anterior Chamber Lens Styles M3-M-5 and Symmetrical Multiflex Anterior Chamber Lens Styles MT-3-MT-7 on p. 2, pp. 1, 2 & 6, Oct. 1982, 623-6.

Primary Examiner—Ronald L. Frinks
Attorney, Agent, or Firm—Henry Sternberg

[57] ABSTRACT

An intraocular lens suitable for use in the posterior chamber of a human eye with position-fixation legs suitable for individually making contact with the ciliary sulcus of the eye at two spaced points thereof. The legs preferably are of polymethylmethacrylate with portions extending counterclockwise and clockwise with respect to the optic to provide sufficient resilience of the free end portion of each leg with respect to the optic to prevent damage to the ciliary sulcus.

2 Claims, 4 Drawing Figures

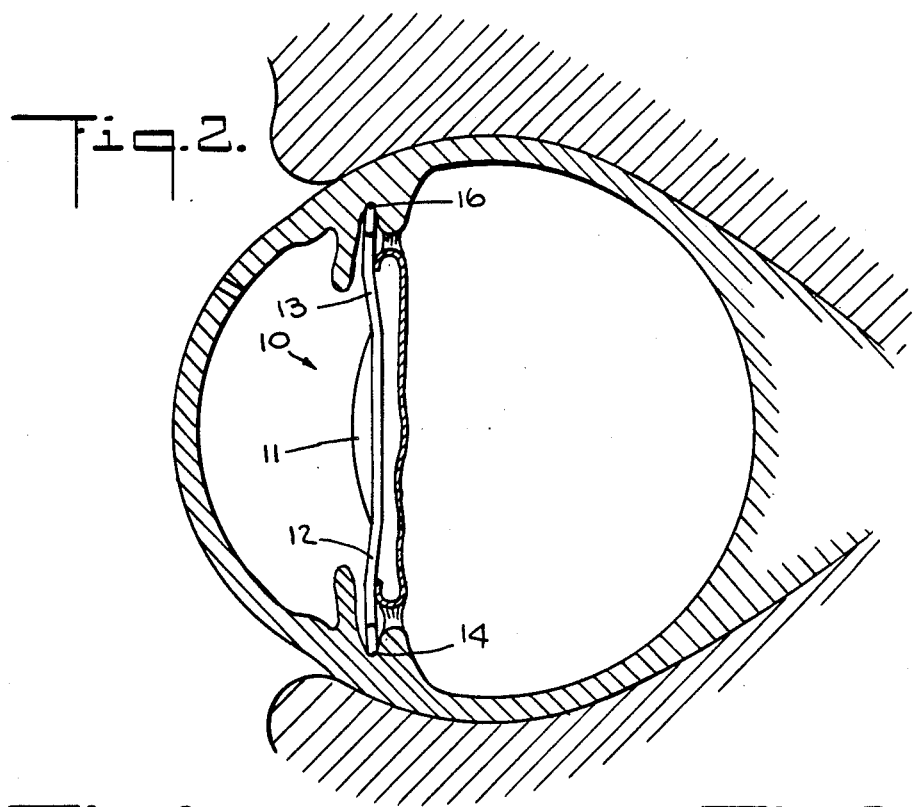
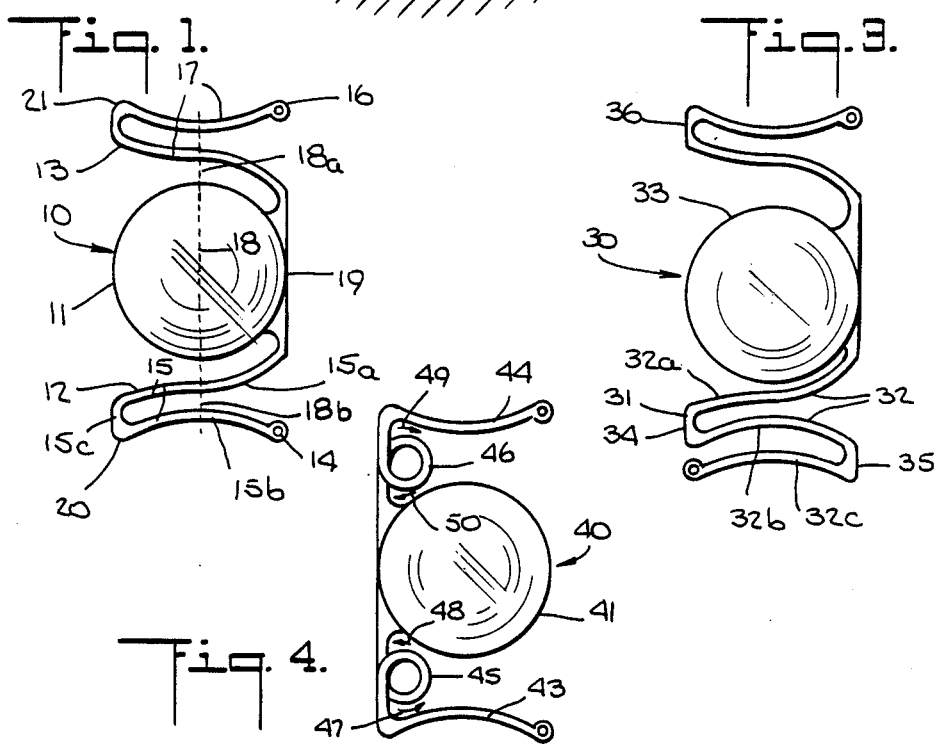

INTRAOCULAR LENS

This is a continuation of co-pending application Ser. No. 465,573 filed on Feb. 10, 1983, now abandoned.

This invention relates to intraocular lenses of the type suitable for use as an artifical lens in the interior of a human eys, and, more particularly, to intraocular lenses of the type suitable for use in the posterior chamber of the eye.

Heretofore, various lenses have been proposed for use in the anterior or posterior chamber. Prior lenses have generally not been suitable for seating in the ciliary sulcus of the posterior chamber because the position-fixation means of the lenses frequently damaged the tissues of the ciliary sulcus.

One prior lens has been proposed for seating in the ciliary sulcus of the posterior chamber with position-fixation means of polypropylene, which position-fixation means of polypropylene are sufficiently flexible for such seating. However, there are substantial concerns in the medical community about the biological inertness, the ability to resist aging e.g. resistance to cracking, discoloration and stiffening of polypropylene. Thus, there is the fear that the polypropylene position-fixation means of the lens referred to above may cause damage to the eye. Polymethylmethacrylate, on the other hand, is a material of proven biological inertness and good aging characteristics. Position-fixation means of this material, however, is not as flexible as position-fixation means of polypropylene and, therefore, polymethylmethacrylate was not believed to be useful for haptics seating in the ciliary sulcus of the posterior chamber.

It is an object of the present invention therefore to provide a new and improved intraocular lens which avoids one or more of the disadvantages and limitations of prior such lenses.

It is another object of the invention to provide a new and improved intraocular lens which is suitable for use in the posterior chamber of the eye.

It is another object of the invention to provide a new and improved intraocular lens which is suitable for seating in the ciliary sulcus of the posterior chamber of the eye.

In accordance with the invention, an intraocular lens suitable for use as an artificial lens in the interior of a human eye comprises a light-focusing lens body. The lens also includes first and second position-fixation means individually joined to the lens body and extending outwardly from the lens body for seating in interior portions of an eye. At least one of the position-fixation means comprises a leg extending outwardly from the lens body and having a free end portion. The leg extending from the lens body to the free end portion includes a portion extending generally in at least two opposite senses with respect to the lens body to provide resilience of the free end portion with respect to the lens body.

Also in accordance with the invention, an intraocular lens suitable for use as an artificial lens in the interior of a human eye comprises a light-focusing lens body and position-fixation means joined to and extending outwardly from the lens body for seating in interior portions of the eye. The position-fixation means comprises (a) a first resilient leg portion extending outwardly from the lens body, (b) a second leg portion extending transversely with respect to the first leg portion and having at least one contact point for seating in an interior portion of an eye, and (c) spring means located intermediate the lens body and the contact point for deceasing the resistance of the position-fixation means to flexing movement of the contact point with respect to the lens body.

For a better understanding of the present invention, together with other and further objects thereof, reference is made to the following description taken in connection with the accompanying drawings, and its scope will be pointed out in the appended claims.

FIG. 1 is a diagrammatic plan view of an embodiment of the present invention intended for fixation in the ciliary sulcus of the posterior chamber of the eye;

FIG. 2 is a side elevational view of the FIG. 1 lens positioned within the eye, shown in section;

FIG. 3 is a diagrammatic plan view of another embodiment of the invention also intended for fixation in the ciliary sulcus of the posterior chamber of the eye; and FIG. 4 is a diagrammatic plan view of another embodiment of the invention intended for fixation in the ciliary sulcus of the posterior chamber of the eye.

Referring now more particularly to FIG. 1 of the drawings, an intraocular lens 10 suitable for use as an artificial lens in the interior of a human eye comprises a light-focusing lens body or optic 11. The optic 11 may be constructed of any biologically inert and transparent material for optical correction such as polymethylmethacrylate, quartz, ophthalmic glass, and other materials known in the art. The lens includes first and second position-fixation means 12, 13 individually joined to the lens body 11 and extending outwardly from the lens body for seating in interior portions of an eye. The position fixation means 12, 13 preferably are of polymethylmethacrylate.

At least one of the position-fixation means 12, 13 comprises a leg 12 extending outwardly from the lens body 10 and having a free end portion 14. The leg 12 extends from the body to the free end portion 14 including a portion 15 extending generally in at least two predetermined opposite senses with respect to the lens body 11 to provide resilience of the free end portion with respect to the lens body 11.

The other of the position-fixation means 12, 13 comprises another leg 13 extending outwardly from the lens body 11 and having a free end portion 16. The other leg 16 extends from the lens body 11 to the free end portion 16 thereof including a portion 17 extending generally in at least two predetermined opposite senses with respect to the lens body to provide resilience of the free end portion 16 of the other leg 13 with respect to the lens body.

At least the one leg 12 of the position-fixation means 12, 13 has a first portion 15a extending in a generally counterclockwise sense with respect to the lens body and a second portion 15b extending in a generally clockwise sense with respect to the lens body 11. The position fixation means comprising legs 12, 13 extend from the same lateral side of the lens body 11 with respect to a predetermined equator 18, represented in broken-line construction, of the lens body 11. The legs 12, 13 individually have free end portions 14, 16 on the same lateral side 19 of the lens body 11. The leg 12 has two spaced contact points 14, 20 for seating in the ciliary sulcus of the posterior chamber of the eye. The leg 13 has two contact spaced points 16, 21 for seating in the ciliary suicus of the eye, as represented in FIG. 2. The portion 15 including a reversal of sense portion 15c comprises a compression spring and similarly portion 17 comprises a compression spring.

As represented in FIG. 2, the legs 12, 13 may be seated in the ciliary sulcus of the eye and the portion 15 of the leg 12 and the portion 17 of the leg 13 provide sufficient resilience of the free end portions 14, 16 with respect to the lens body that the tissues of the ciliary sulcus are not damaged.

As represented in FIG. 1, an imaginary longitudinal extension 18a, 18b of the equator 18 of the lens body 11 intersects, at least twice, the leg portion 15 extending generally in at least two predetermined opposite senses with respect to the lens body 11 and also intersects, at least twice, the leg portion 17 extending generally in at least two predetermined opposite senses with respect to the lens body.

Referring now more particularly to FIG. 3, there is represented a lens 30 similar to the lens 10 of FIG. 1. The lens 30 has, however, position-fixation means 31 comprising a generally S-shaped spring portion having a leg which extends from the lens body 33 to a free end portion including a portion 32 extending generally in at least two predetermined opposite senses but with two general reversals of sense. That is, the portion 32a extends generally counterclockwise of the lens body 33 with a reversal of sense occurring at portion 34. The portion 32b extends generally clockwise of the lens body 33 with a reversal of sense at portion 35. The portion 32c extends generally in a counterclockwise sense with respect to the lens body 33. The position-fixation means 36 is similar to the position-fixation means 13 of the FIG. 1 lens. Since the position-fixation means 31 has three generally parallely curved limb portions 32a, 32b, 32c and two reversals of sense at portions 34, 35, the lens body 33 is positioned more closely to the position-fixation means 31 than to the position-fixation means 36 so that the lens body will be at the proper vertical position in the eye when the position-fixation means 31, 36 are seated in the ciliary sulcus of the eye. Each of the three limb portions 32a, 32b, 32c have an outwardly concave portion substantially parallel to the corresponding portion of each of the other limb portions and the outermost limb portion 32c has a pair of contact points on opposite sides of its concave portion for seating the lens in the eye. The innermost limb portion 32a is further provided with an inwardly concave portion intermediate the respective outwardly concave portion and the end connected to the lens body 33. As shown in FIG. 3 the inwardly concave portion is generally parallel in curvature to the curvature of the portion of the periphery of the lens body adjacent thereto.

Referring now more particularly to FIG. 4, there is represented a lens 40 having a lens body 41 with position-fixation means 43, 44. Each of the position fixation means 43, 44 includes an intermediate resilient loop portion 45, 46, respectively, extending generally in at least two predetermined opposite senses with respect to the lens body 41, namely the clockwise and counter-clockwise senses represented by arrows 47, 48, respectively, and 49, 50, respectively. The resilient loop portions 45, 46 individually comprise compression springs.

The lens 40 is otherwise similar to the lens 10 of the FIG. 1 embodiment.

While there have been described what are presently considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. An intraocular lens suitable for use as an artificial lens in the interior of a human eye, comprising:
    a light-focusing lens body;
    first and second position-fixation means individually joined to said lens body and extending outwardly from said lens body for seating in interior portions of an eye;
    at least one of said position-fixation means comprising a generally S-shaped portion connected at one of its ends to said lens body, said generally S-shaped spring portion comprising three generally parallely curved limbs positioned with respect to said lens body such that an imaginary longitudinal extension of a predetermined equator of said lens body intersects each of said three limbs; each of said three limbs having an outwardly concave portion substantially parallel to the corresponding portion of each of the other of said three limbs, the outermost one of said three limbs having a pair of contact points on opposite sides of the respective concave portion for seating the lens in the eye, and the innermost one of said three limbs having an inwardly concave portion intermediate the respective outwardly concave portion thereof and said one end thereof connected to said lens body, said inwardly concave portion being generally parallel in curvature to the curvature of the portion of the periphery of said lens body adjacent thereto.

2. A lens in accordance with claim 1, in which the other of said position-fixation means comprises a generally S-shaped spring portion connected at one of its ends to said lens body, said last mentioned generally S-shaped spring portion comprising three generally parallely curved limbs positioned with respect to said lens body such that an imaginary longitudinal extension of a predetermined equator of said lens body intersects each of said last mentioned three limbs;
    each of said three limbs of said other of said position-fixation means having an outwardly concave portion substantially parellel to the corresponding portion of each of the other of said last mentioned three limbs, and the outermost one of said last mentioned three limbs having a pair of contact points on opposite sides of the respective concave portion for seating the lens in the eye and the innermost one of said last mentioned three limbs having an inwardly concave portion intermediate the respective outwardly concave portion thereof and said one end thereof connected to said lens body, said inwardly concave portion being generally parallel in curvature to the curvature of the portion of the periphery of said lens body adjacent thereto.

* * * * *

UNITED STATES PATENT AND TRADEMARK OFFICE
CERTIFICATE OF CORRECTION

PATENT NO. : 4,676,794

DATED : June 30, 1987

INVENTOR(S) : Charles D. Kelman

It is certified that error appears in the above-identified patent and that said Letters Patent is hereby corrected as shown below:

Column 4, claim 1, line 20, after "S-shaped" insert -- spring -- .

Signed and Sealed this

First Day of December, 1987

*Attest:*

DONALD J. QUIGG

*Attesting Officer*     *Commissioner of Patents and Trademarks*